(12) United States Patent
Baaijens et al.

(10) Patent No.: US 9,392,651 B2
(45) Date of Patent: Jul. 12, 2016

(54) LIGHTING METHODS AND APPARATUS WITH SELECTIVELY APPLIED FACE LIGHTING COMPONENT

(71) Applicant: KONINKLIJKE PHILIPS N.V., Eindhoven (NL)

(72) Inventors: Johannes Petrus Wilhelmus Baaijens, Eindhoven (NL); Lucas Leo Desiree Van Der Poel, Waalre (NL); Lucas Josef Maria Schlangen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/391,287

(22) PCT Filed: Apr. 5, 2013

(86) PCT No.: PCT/IB2013/052735
§ 371 (c)(1),
(2) Date: Oct. 8, 2014

(87) PCT Pub. No.: WO2013/153495
PCT Pub. Date: Oct. 17, 2013

(65) Prior Publication Data
US 2015/0061506 A1    Mar. 5, 2015

Related U.S. Application Data

(60) Provisional application No. 61/622,596, filed on Apr. 11, 2012.

(51) Int. Cl.
| H05B 37/02 | (2006.01) |
| H05B 33/08 | (2006.01) |
| G02F 1/29 | (2006.01) |

(52) U.S. Cl.
CPC ........ *H05B 33/08* (2013.01); *G02F 1/29* (2013.01); *H05B 37/0218* (2013.01); *Y02B 20/46* (2013.01)

(58) Field of Classification Search
CPC .. H05B 37/02; H05B 37/029; H05B 37/0218; H05B 37/0227; H05B 33/0815; H05B 33/0803; H05B 33/0845; H05B 33/08; Y02B 20/46; Y02B 20/48; F21S 8/04; F21Y 2101/02; F21K 9/00; G02F 1/29
USPC ......... 315/294, 152, 153, 297, 307, 312, 318; 362/227, 236, 613, 147, 131, 153
See application file for complete search history.

(56) References Cited

U.S. PATENT DOCUMENTS 7,828,465 B2 * 11/2010 Roberge ................ F21S 8/033
362/147
8,232,745 B2 * 7/2012 Chemel ................ F21V 29/763
315/291

(Continued)

FOREIGN PATENT DOCUMENTS

| CN | 102027807 A | 4/2011 |
| EP | 677697 A1 | 10/1995 |

(Continued)

*Primary Examiner* — Haissa Philogene
(74) *Attorney, Agent, or Firm* — Meenakshy Chakravorty

(57) ABSTRACT

Disclosed are methods and apparatus that enable selectively applied face lighting and, optionally, selectively applied task lighting, for example, in daylight-responsive lighting systems and/or therapeutic lighting systems. The face lighting may be selectively provided in a plurality of modes to one or more user segments, and, optionally, only provided to those user segments having a human presence.

18 Claims, 6 Drawing Sheets

(56) References Cited

U.S. PATENT DOCUMENTS

| | | | |
|---|---|---|---|
| 8,779,669 B2 * | 7/2014 | Ramer | H05B 37/0209 315/153 |
| 2007/0297354 A1 | 12/2007 | Ishiyama et al. | |
| 2010/0148688 A1 | 6/2010 | Hikmet et al. | |
| 2010/0149444 A1 | 6/2010 | Hikmet et al. | |
| 2011/0270446 A1 * | 11/2011 | Scharf | F24F 11/0001 700/282 |
| 2015/0102747 A1 * | 4/2015 | Wang | H02J 3/14 315/294 |
| 2015/0289347 A1 * | 10/2015 | Baaijens | H05B 39/044 315/294 |
| 2015/0373806 A1 * | 12/2015 | Vissenberg | H05B 33/0872 315/151 |

FOREIGN PATENT DOCUMENTS

| | | |
|---|---|---|
| JP | 2010123534 A | 6/2010 |
| JP | 2010192189 A | 9/2010 |
| JP | 2010231924 A | 10/2010 |
| WO | 2008126049 A | 10/2008 |

* cited by examiner

LIGHTING METHODS AND APPARATUS WITH SELECTIVELY APPLIED FACE LIGHTING COMPONENT

CROSS-REFERENCE TO PRIOR APPLICATIONS

This application is the U.S. National Phase application under 35 U.S.C. §371 of International Application No. PCT/IB2013/052735, filed on Apr. 5, 2013, which claims the benefit of U.S. Provisional Patent Application No. 61/622596, filed on Apr. 11, 2012. These applications are hereby incorporated by reference herein.

The present invention is directed generally to methods and apparatus for controllable lighting. More particularly, various inventive aspects disclosed herein relate to lighting methods and apparatus having selectively applied face lighting.

Daylight-responsive lighting systems have been implemented in various environments, such as offices, hotels, and retail stores. The Daylight-responsive lighting systems include one or more light sensors that detect light levels within a lighting environment. The light output of one or more lighting fixtures in the lighting environment is adjusted in response to detected light conditions. For example, it may be desirable to decrease the light output of lighting fixtures when significant natural daylight is provided to the environment, for example via windows or skylights, in order to save energy, provide a more pleasing environment, and/or for other reasons. Also, for example, it may be desirable to increase the light output of lighting fixtures when little or no natural daylight is provided (e.g., at night, cloudy conditions, or when daylight blocking elements such as blinds are utilized) to maintain a desired level of light output in the lighting environment. Although such lighting systems enable adjustment of light output of one or more lighting fixtures that is dependent on daylight conditions, they may have one or more drawbacks. For example, in certain environments (e.g., a meeting room), when daylight is entering the environment and lighting fixtures within the environment are dimmed due to the entering daylight, there is too high of a contrast between the daylight from a bright window and the objects (e.g., humans) that are positioned in front of the window—when those objects are viewed in front of the window. Such high contrast may make viewing of the object positioned in front of the window difficult for a user. For example, only a silhouette of a person positioned in front of a bright window will be visible by a viewer opposite the window and facial expressions will not be fully visible, which may make conversation difficult.

Various therapeutic lighting systems have also been utilized. For example, therapeutic lighting systems have been utilized for therapy for seasonal depression, therapy for jetlag by flying, therapy for social jetlag, etc. Such therapeutic lighting systems often include a lighting fixture that a user must sit or stand in front of for a period of time for therapy purposes. Such therapeutic lighting systems may have one or more drawbacks such as, for example, the requirement of dedicated spaces or locations where the user has to sit down and/or stand for an extended period of time. Also, for example, the bright therapeutic light may be bothersome to other individuals present that do not need the light therapy.

Thus, there is a need in the art to provide methods and apparatus related to face lighting that may optionally be utilized to overcome one or more drawbacks of existing daylight-responsive lighting systems and/or existing therapeutic lighting systems.

Applicants have recognized and appreciated that it would be beneficial to provide lighting methods and apparatus having independently adjustable face and task lighting with face lighting being applied selectively. In view of the foregoing, various embodiments and implementations of the present invention are directed to methods and apparatus for controllable lighting.

For example, methods and apparatus are disclosure that have selectively applied face lighting and, optionally, selectively applied task lighting. The face lighting may be selectively provided to one or more user segments. In some embodiments, the face lighting is only provided to those user segments having a human presence. The face lighting may be provided in a plurality of modes.

Generally, in one aspect, a method of controlling a task lighting component and a face lighting component of at least one lighting fixture is provided and includes the steps of: monitoring a light level proximal a task area; providing task lighting from at least one lighting fixture over the task area to the task area when the light level proximal the task area is below a threshold value; monitoring each of a plurality of user segments for a human presence, the user segments adjacent the task area and utilized for user interaction with the task area; and providing face lighting from the at least one lighting fixture over the task area only to the user segments having the human presence.

In some embodiments, the task lighting is distinct from the face lighting in at least one of intensity, spectral composition, and dynamic behavior. In some versions of those embodiments, various attributes and characteristics of the face lighting and/or task lighting can be set independently for at least one of the user segments via a user interface.

In some embodiments, in response to identifying at least one of a predetermined intensity of incoming daylight and a predetermined direction of the incoming daylight, the face lighting is automatically provided to the user segments that are on the side of the lighting fixture where the daylight originates.

In some embodiments, a task lighting level of the task lighting is proportional to the light level proximal the task area.

In some embodiments, an origination direction of the face lighting directed toward each of the user segments is adjustable.

In some embodiments, an origination direction of the face lighting directed toward each of the user segments includes at least a first component primarily directed about a first axis and a second component primarily directed about a second axis.

In some embodiments, the step of monitoring each of the user segments includes monitoring reflections of coded light directed at each of the user segments.

In some embodiments, each of the user segments include at least one chair sitting area adjacent the task area.

In some embodiments, in a first mode, only the user segments having the human presence and interposed between the task area and a window contributing to the light level are provided with the face lighting. In some versions of those embodiments, in a second mode, all the user segments having the human presence are provided with the face lighting. Optionally, in the first mode, a ratio of a face surface lux to a task surface lux is less than one, the face surface lux taken at a face surface in each of the user segments and the task surface lux taken at the task surface. Optionally, in the second mode, the ratio of the face surface lux to the task surface lux is tunable within a second range, the second range including values greater than one.

In some embodiments, the task lighting is generated from a first group of LEDs facing the task area and the face lighting is generated from a second group of LEDs facing the user segments.

Generally, in another aspect, a method of controlling a task lighting component and a face lighting component of at least one lighting fixture is provided and includes the steps of: monitoring a light level proximal a task area; providing task lighting to the task area when the light level proximal the task area is below a threshold value; providing, in a first mode, face lighting to at least window user segments of a plurality of user segments; and providing face lighting to at least one of the user segments in a second mode. The user segments are adjacent the task area and are utilized for user interaction with the task area and the window user segments are interposed between the task area and a window contributing to the light level. In the second mode a ratio of a face surface lux to a task surface lux is at least two times greater than it is in the first mode. The first surface lux taken at a face surface in each of the user segments and the task surface lux taken at the task surface.

The method may further include monitoring each of the user segments for a human presence and providing face lighting only to the user segments having the human presence.

In some embodiments, in the first mode, the ratio of a face surface lux to a task surface lux is less than one. In some versions of those embodiments, in the second mode, the ratio of the face surface lux to the task surface lux is tunable within a second range, the second range including values greater than one.

In some embodiments, in the first mode, the ratio of the face surface lux to the task surface lux is less than 0.5.

In some embodiments, in the first mode, the ratio of the face surface lux to the task surface lux is tunable from 0 to at least 0.2.

In some embodiments, in the second mode, the ratio of the face surface lux to the task surface lux is tunable from 0 to at least 2.

In still another aspect, the invention focuses on a method of independently controlling a task lighting component and a face lighting component of at least one lighting fixture, wherein said task lighting is distinct from said face lighting in at least one of intensity, spectral composition, and dynamic behavior. The method includes providing task lighting from at least one lighting fixture over said task area to said task area; monitoring at least two of a plurality of user segments for a human presence, said user segments adjacent said task area and utilized for user interaction with said task area; and providing face lighting from said at least one lighting fixture over said task area only to said user segments having said human presence.

Generally, in yet another aspect, a lighting fixture having a task lighting component and a face lighting component is provided. The lighting fixture includes a plurality of task lighting LEDs selectively providing a task light output in a downward direction below the lighting fixture and a plurality of face lighting LEDs providing a face light output in a direction peripherally of the lighting fixture. The lighting fixture also includes at least one controller controlling the task lighting LEDs and the face lighting LEDs. The controller receives daylight sensing signals and user segment presence sensing signals. The user segment presence sensing signals are indicative of which of a plurality of user segments adjacent a task area are occupied by a human. The controller activates a plurality of the task lighting LEDs when the daylight sensing signals are indicative of a light level below a threshold value. The controller activates a plurality of the face lighting LEDs in a first mode and in a second mode, wherein in the second mode a ratio of a face surface lux to a task surface lux of light output generated by the face lighting LEDs is at least two times greater than it is in the first mode. The controller activates only the face lighting LEDs providing the face lighting output in a direction toward the user segments having the human presence.

In some embodiments, the lighting fixture further includes at least one daylight sensor providing the daylight sensing signals and at least one presence sensor providing the presence sensing signals.

As used herein for purposes of the present disclosure, the term "LED" should be understood to include any electroluminescent diode or other type of carrier injection/junction-based system that is capable of generating radiation in response to an electric signal. Thus, the term LED includes, but is not limited to, various semiconductor-based structures that emit light in response to current, light emitting polymers, organic light emitting diodes (OLEDs), electroluminescent strips, and the like. In particular, the term LED refers to light emitting diodes of all types (including semi-conductor and organic light emitting diodes) that may be configured to generate radiation in one or more of the infrared spectrum, ultraviolet spectrum, and various portions of the visible spectrum (generally including radiation wavelengths from approximately 400 nanometers to approximately 700 nanometers). Some examples of LEDs include, but are not limited to, various types of infrared LEDs, ultraviolet LEDs, red LEDs, blue LEDs, green LEDs, yellow LEDs, amber LEDs, orange LEDs, and white LEDs (discussed further below). It also should be appreciated that LEDs may be configured and/or controlled to generate radiation having various bandwidths (e.g., full widths at half maximum, or FWHM) for a given spectrum (e.g., narrow bandwidth, broad bandwidth), and a variety of dominant wavelengths within a given general color categorization.

For example, one implementation of an LED configured to generate essentially white light (e.g., a white LED) may include a number of dies which respectively emit different spectra of electroluminescence that, in combination, mix to form essentially white light. In another implementation, a white light LED may be associated with a phosphor material that converts electroluminescence having a first spectrum to a different second spectrum. In one example of this implementation, electroluminescence having a relatively short wavelength and narrow bandwidth spectrum "pumps" the phosphor material, which in turn radiates longer wavelength radiation having a somewhat broader spectrum.

It should also be understood that the term LED does not limit the physical and/or electrical package type of an LED. For example, as discussed above, an LED may refer to a single light emitting device having multiple dies that are configured to respectively emit different spectra of radiation (e.g., that may or may not be individually controllable). Also, an LED may be associated with a phosphor that is considered as an integral part of the LED (e.g., some types of white LEDs). In general, the term LED may refer to packaged LEDs, non-packaged LEDs, surface mount LEDs, chip-on-board LEDs, T-package mount LEDs, radial package LEDs, power package LEDs, LEDs including some type of encasement and/or optical element (e.g., a diffusing lens), etc.

The term "light source" should be understood to refer to any one or more of a variety of radiation sources, including, but not limited to, LED-based sources (including one or more LEDs as defined above), incandescent sources (e.g., filament lamps, halogen lamps), fluorescent sources, phosphorescent sources, high-intensity discharge sources (e.g., sodium vapor, mercury vapor, and metal halide lamps), lasers, and other types of electroluminescent sources.

A given light source may be configured to generate electromagnetic radiation within the visible spectrum, outside the visible spectrum, or a combination of both. Hence, the terms "light" and "radiation" are used interchangeably herein. Additionally, a light source may include as an integral component one or more filters (e.g., color filters), lenses, or other optical components. Also, it should be understood that light sources may be configured for a variety of applications, including, but not limited to, indication, display, and/or illumination. An "illumination source" is a light source that is particularly configured to generate radiation having a sufficient intensity to effectively illuminate an interior or exterior space. In this context, "sufficient intensity" refers to sufficient radiant power in the visible spectrum generated in the space or environment (the unit "lumens" often is employed to represent the total light output from a light source in all directions, in terms of radiant power or "luminous flux") to provide ambient illumination (i.e., light that may be perceived indirectly and that may be, for example, reflected off of one or more of a variety of intervening surfaces before being perceived in whole or in part).

The terms "spectrum" or "spectral composition" should be understood to refer to any one or more frequencies (or wavelengths) of radiation produced by one or more light sources. Accordingly, the term "spectrum" refers to frequencies (or wavelengths) not only in the visible range, but also frequencies (or wavelengths) in the infrared, ultraviolet, and other areas of the overall electromagnetic spectrum. Also, a given spectrum may have a relatively narrow bandwidth (e.g., a FWHM having essentially few frequency or wavelength components) or a relatively wide bandwidth (several frequency or wavelength components having various relative strengths). It should also be appreciated that a given spectrum may be the result of a mixing of two or more other spectra (e.g., mixing radiation respectively emitted from multiple light sources).

For purposes of this disclosure, the term "color" is used interchangeably with the terms "spectrum" and "spectral composition." However, the term "color" generally is used to refer primarily to a property of radiation that is perceivable by an observer (although this usage is not intended to limit the scope of this term). Accordingly, the terms "different colors" implicitly refer to multiple spectra having different wavelength components and/or bandwidths. It also should be appreciated that the term "color" may be used in connection with both white and non-white light.

The term "color temperature" generally is used herein in connection with white light, although this usage is not intended to limit the scope of this term. Color temperature essentially refers to a particular color content or shade (e.g., reddish, bluish) of white light. The color temperature of a given radiation sample conventionally is characterized according to the temperature in degrees Kelvin (K) of a black body radiator that radiates essentially the same spectrum as the radiation sample in question. Black body radiator color temperatures generally fall within a range of from approximately 700 degrees K (typically considered the first visible to the human eye) to over 10,000 degrees K; white light generally is perceived at color temperatures above 1500-2000 degrees K.

The term "lighting fixture" or "luminaire" are used interchangeably herein to refer to an implementation or arrangement of one or more lighting units in a particular form factor, assembly, or package. The term "lighting unit" is used herein to refer to an apparatus including one or more light sources of same or different types. A given lighting unit may have any one of a variety of mounting arrangements for the light source(s), enclosure/housing arrangements and shapes, and/or electrical and mechanical connection configurations. Additionally, a given lighting unit optionally may be associated with (e.g., include, be coupled to and/or packaged together with) various other components (e.g., control circuitry) relating to the operation of the light source(s). An "LED-based lighting unit" refers to a lighting unit that includes one or more LED-based light sources as discussed above, alone or in combination with other non LED-based light sources. A "multi-channel" lighting unit refers to an LED-based or non LED-based lighting unit that includes at least two light sources configured to respectively generate different spectrums of radiation, wherein each different source spectrum may be referred to as a "channel" of the multi-channel lighting unit.

The term "controller" is used herein generally to describe various apparatus relating to the operation of one or more light sources. A controller can be implemented in numerous ways (e.g., such as with dedicated hardware) to perform various functions discussed herein. A "processor" is one example of a controller which employs one or more microprocessors that may be programmed using software (e.g., microcode) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media (generically referred to herein as "memory," e.g., volatile and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present invention discussed herein. The terms "program" or "computer program" are used herein in a generic sense to refer to any type of computer code (e.g., software or microcode) that can be employed to program one or more processors or controllers.

The term "network" as used herein refers to any interconnection of two or more devices (including controllers or processors) that facilitates the transport of information (e.g. for device control, data storage, data exchange, etc.) between any two or more devices and/or among multiple devices coupled to the network. As should be readily appreciated, various implementations of networks suitable for interconnecting multiple devices may include any of a variety of network topologies and employ any of a variety of communication protocols. Additionally, in various networks according to the present disclosure, any one connection between two devices may represent a dedicated connection between the two systems, or alternatively a non-dedicated connection. In addition to carrying information intended for the two devices, such a non-dedicated connection may carry information not necessarily intended for either of the two devices (e.g., an open network connection). Furthermore, it should be readily appreciated that various networks of devices as discussed herein may employ one or more wireless, wire/cable, and/or fiber optic links to facilitate information transport throughout the network.

The term "user interface" as used herein refers to an interface between a human user or operator and one or more devices that enables communication between the user and the device(s). Examples of user interfaces that may be employed in various implementations of the present disclosure include, but are not limited to, switches, potentiometers, buttons, dials, sliders, a mouse, keyboard, keypad, various types of game controllers (e.g., joysticks), track balls, display screens, various types of graphical user interfaces (GUIs), touch screens, microphones and other types of sensors that may receive some form of human-generated stimulus and generate a signal in response thereto.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

In the drawings, like reference characters generally refer to the same parts throughout the different views. Also, the drawings are not necessarily to scale, emphasis instead generally being placed upon illustrating the principles of the invention.

In the following detailed description, for purposes of explanation and not limitation, representative embodiments disclosing specific details are set forth in order to provide a thorough understanding of the claimed invention. However, it will be apparent to one having ordinary skill in the art having had the benefit of the present disclosure that other embodiments according to the present teachings that depart from the specific details disclosed herein remain within the scope of the appended claims. Moreover, descriptions of well-known apparatus and methods may be omitted so as to not obscure the description of the representative embodiments. Such methods and apparatus are clearly within the scope of the claimed invention. For example, various embodiments of the approach disclosed herein are particularly suited for a lighting system that includes a face lighting component, a task lighting component, and at least one sensor to selectively provide task lighting and selectively provide face lighting in accordance with at least two modes. Accordingly, for illustrative purposes, the claimed invention is discussed in conjunction with such a lighting system. However, other configurations and applications are contemplated without deviating from the scope or spirit of the claimed invention. For example, aspects may be implemented in other lighting systems that only include a single mode. Also, for example, aspects may be implemented in other lighting systems that only include a face lighting component.

Figure 1:
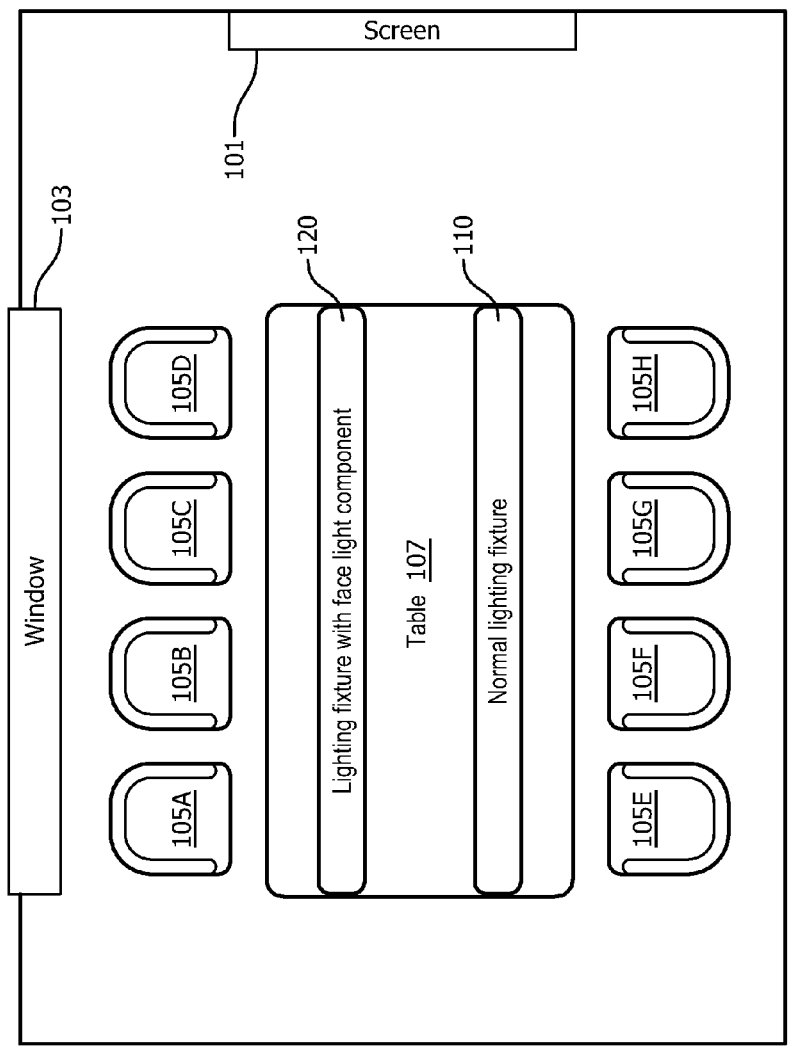
FIG. 1 illustrates a top plan view of a meeting room having an embodiment of a lighting system; no artificial light is present and a lighting fixture with a face light component is switched off and a normal lighting fixture is also switched off.
Figure 2:
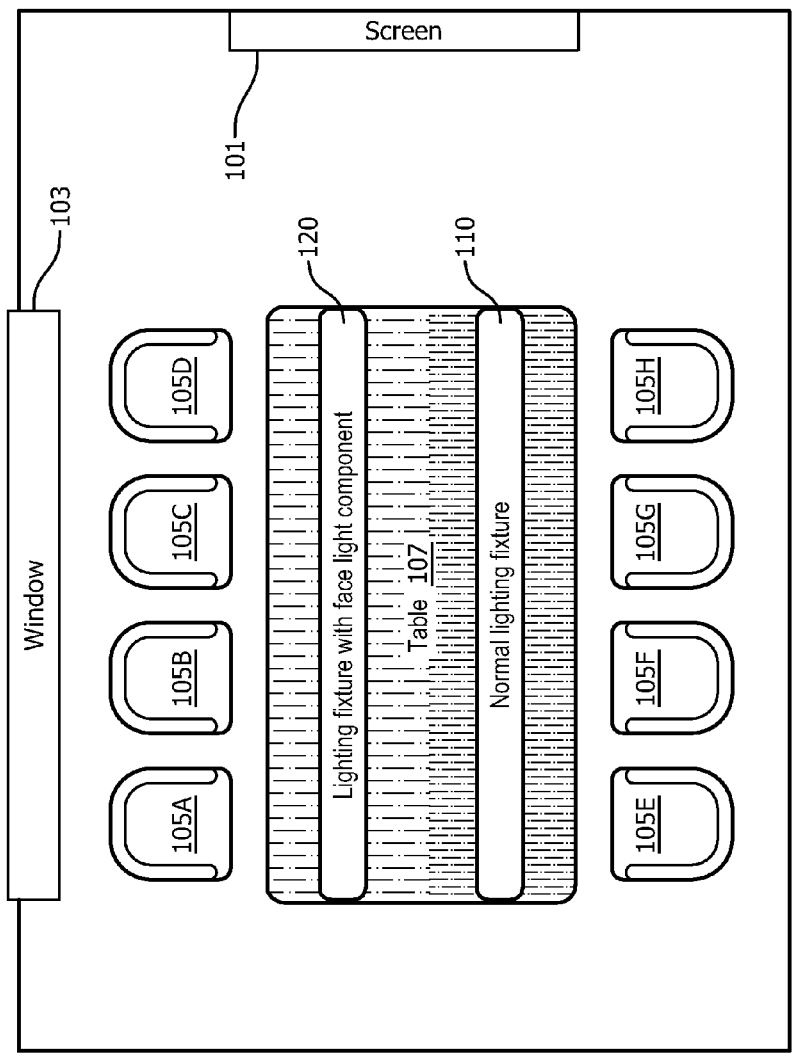
FIG. 2 illustrates a top plan view of the meeting room and the first embodiment of the lighting system; a task lighting component of the lighting fixture with the face light component is switched on and the normal lighting fixture is switched off.
Figure 3:
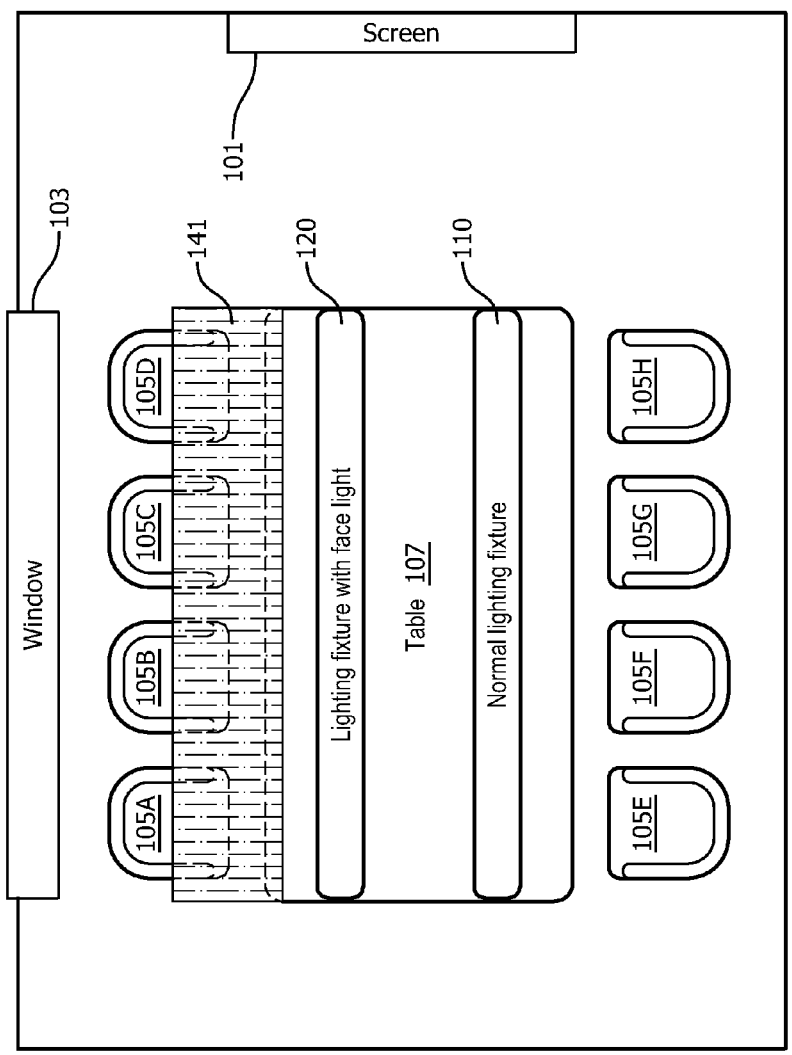
FIG. 3 illustrates a top plan view of the meeting room and the first embodiment of the lighting system; the task lighting component of the lighting fixture with the face light component is switched off, a facial lighting component of the lighting fixture with the face light component is switched on, and the normal lighting fixture is switched off.

Referring to FIGS. 1-3, a top plan view of a meeting room is illustrated. The meeting room includes a screen 101 along a portion of a first wall thereof that may be utilized as a projector screen for presentations. The meeting room also includes a window 103 along a portion of a second wall thereof that provides for viewing of an outside environment located exterior to the meeting room. When present, natural daylight from the outside environment passes through the window 103 and provides lighting to the meeting room. Inside the meeting room are eight chairs 105A-H positioned around a rectangular table 107.

Figure 5:
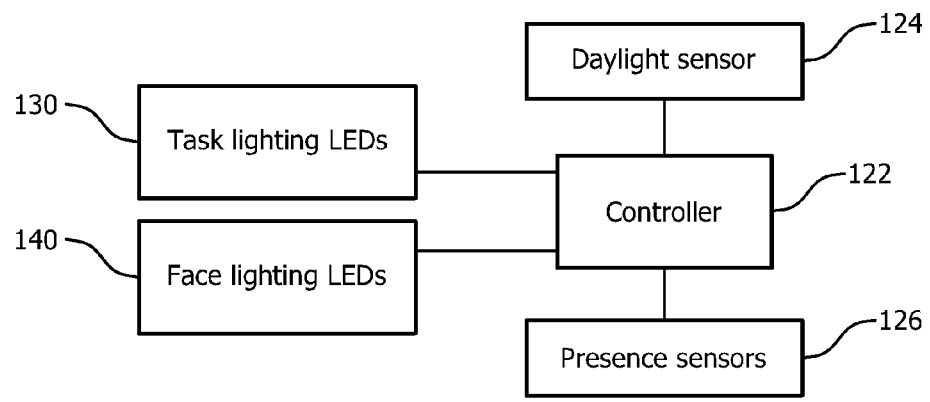
FIG. 5 illustrates a block diagram of the lighting fixture with the face light component of the embodiment of the lighting system of FIGS. 1-4.

A lighting fixture 120 is present in the meeting room positioned above the rectangular table 107. Referring to FIG. 5, the lighting fixture 120 includes at least one controller 122 in communication with at least one daylight sensor 124 and at least one presence sensor 126. The lighting fixture also includes a plurality of task lighting LEDs 130 in communication with the controller 122 and a plurality of face lighting LEDs 140 in communication with the controller 122. The task lighting LEDs 130 selectively generate a light output that is directed toward and illuminates at least a portion of the table 107. The face lighting LEDs 140 selectively generate a light output that is directed toward and illuminates at least a portion of the area adjacent chairs 105A-D (e.g., at least the area that would be occupied by faces of humans that are sitting in the chairs 105A-D).

The controller 122 controls the status of task lighting LEDs 130 and face lighting LEDs 140. For example, the controller 122 may be in communication with one or more LED drivers powering task lighting LEDs 130 to control whether the task lighting LEDs 130 are generating light output and, if generating light output, to optionally control one or more characteristics of the light output generated by the task lighting LEDs 130. Also, for example, the controller 122 may be in communication with one or more LED drivers powering face lighting LEDs 140 to control whether the face lighting LEDs 140 are generating light output and, if generating light output, to optionally control one or more characteristics of the light output generated by the face lighting LEDs 140. In some embodiments aspects of the controller 122 may be at least partially integrated in one or more LED drivers powering the LEDs 130 and/or 140.

Generally speaking, the daylight sensor 124 measures one or more values indicative of the daylight level proximal the table 107 and communicates signals indicative of such values to the controller 122. Also, generally speaking, the presence sensor 126 measures one or more values indicative of whether a human is present in one or more of the seats 105A-D and communicates signals indicative of such values to the controller 122. The daylight sensor 124 may include one or more photosensors. The presence sensor 126 may include one or more passive infrared (PIR) sensors in some embodiments. In some embodiments the presence sensor 126 may include one or more sensors detecting changes in coded light generated by the lighting fixture 120 (e.g., change in coded light generated by the face lighting LEDs 140). For example, the presence sensor 126 may detect changes in reflected coded light generated by face lighting LEDs 140 when a human is sitting in one of the chairs 105A-D compared to when nobody is sitting in the chairs 105A-D. The face lighting LEDs 140 may optionally generate a plurality of coded light transmissions to determine which chair or group of chairs 105A-D is occupied. For example, those LEDs of face lighting LEDs 140 generating light output that is directed toward chair 105A may generate a first coded light, those LEDs of face lighting LEDs 140 generating light output that is directed toward chair 105B may generate a second coded light, those LEDs of face lighting LEDs 140 generating light output that is directed toward chair 105C may generate a third coded light, and those LEDs of face lighting LEDs 140 generating light output that is directed toward chair 105D may generate a fourth coded light. Each coded light may be individually monitored for changes by one or more sensors to determine which of chairs 105A-D are occupied. In some embodiment the presence sensor 126 may include one or more video cameras such as an infrared video camera.

The controller 122, the daylight sensor 124, and the presence sensor 126 may be integrated as a cohesive part of the lighting fixture 120 in some embodiments. For example, the daylight sensor 124 may have exposure to the environment exterior of the lighting fixture 120 and face generally toward the table 107 under lighting fixture 120 and/or generally toward the window 103 to enable sensing of light levels proximal the table 107. Also, for example, the presence sensor 126 may have exposure to the environment exterior of the lighting fixture 120 and the presence sensor 126 may be directed toward one or more of chairs 105A-D to enable sensing of a human presence in such one or more chairs 105A-D. In other embodiments the daylight sensor 124 and/or the presence sensor 126 may be physically separated from other components of the lighting fixture 120. For example, the daylight sensor 124 may be placed on the table 107, integrated into the table 107, or placed on a ceiling of the meeting room. Also, for example, the presence sensor 126 may be placed in the chairs 105A-D or placed on a ceiling of the meeting room. One of ordinary skill in the art, having had the benefit of the present disclosure, will recognize and appreciate that various implementations and/or configurations of one or more daylight sensors and/or presence sensor may be utilized to assist in the application of task lighting and/or face lighting from one or more lighting fixtures.

Referring again to FIGS. 1-3, a lighting fixture 110 without a face lighting component is also present in the meeting room positioned above the rectangular table 107. In some embodiments the lighting fixture 110 may be controlled independently of the lighting fixture 120. For example, in some embodiments the lighting fixture 110 may be manually controlled via a dimming switch. Also, for example, in some embodiments the lighting fixture 110 may include its own daylight sensor and adjust its light output dependent on readings from that daylight sensor. In some other embodiments the lighting fixture 110 and the lighting fixture 120 may be cooperatively controlled. For example, in some embodiment the lighting fixtures 110, 120 may be in network communication with one another and may share daylight sensor readings and/or light settings.

In FIG. 1, no artificial light is present in the meeting room and the lighting fixture 120 is switched off and the lighting fixture 110 is also switched off. This may be the desired state, for example, when nobody is present in the meeting room and/or when a presentation is being presented on the screen 103. A user interface (e.g., a control panel) may be utilized to place the lighting fixtures 110, 120 in the state of FIG. 1. The lighting fixtures 110, 120 may additionally or alternatively be in the state of FIG. 1 in response to no human presence being detected in the room by one or more presence sensors (e.g., presence sensor 126).

In FIG. 2, a task lighting component of the lighting fixture 120 is switched on and the lighting fixture 110 is switched off. The task lighting LEDs 130 of the lighting fixture 120 are providing desired illumination to the table 107. The daylight sensor 124 may measure the light level on the table 107 (or alternatively may measure the light level elsewhere in the meeting room) and the controller 122 adjust the light output intensity of the task lighting LEDs 130 to maintain the light level at a desired level. For example, in some embodiments the light output of one or more of the LEDs 130 may be adjusted based on values from the daylight sensor 124 to maintain the light level on table 107 at approximately 500 lux. The state of FIG. 2 may be the desired state when individuals are present in the meeting room, task lighting on table 107 is desired, and daylight provided through window 103 alone is insufficient to illuminate the table 107 as desired. A user interface (e.g., a control panel) may optionally be utilized to place the lighting fixtures 110, 120 in the state of FIG. 2. In some embodiments the controller 122 will automatically place the lighting fixture 120 in the state of FIG. 2 based on readings from presence sensor 126 and/or daylight sensor 124. Lighting fixture 110 may additionally or alternatively be illuminated. For example, in some embodiments if lighting fixture 110 is illuminated it may be unnecessary to illuminate task lighting LEDs 130 as brightly and/or to even activate task lighting LEDs 130 at all.

In FIG. 3, the task lighting LEDs 130 of the lighting fixture 120 are switched off, the face lighting LEDs 140 of the lighting fixture 120 are switched on, and the lighting fixture 110 is switched off. Desired illumination is being provided to the table 107 via window 103. The daylight sensor 124 may measure the light level on the table 107 (or alternatively may measure the light level elsewhere in the meeting room) to enable the controller 122 to determine whether further illumination via task lighting LEDs 130 is required. Also, the daylight sensor 124 may measure the light level on the table 107 to enable the controller 122 to determine when light intensity from window 103 is sufficient to activate face lighting LEDs 140. The controller 122 may additionally or alternatively look at the status and characteristics of light output from task lighting LEDs 130 and/or lighting fixture 110 (e.g., to deduce the contribution from window 103) and/or other daylight sensor (e.g., aimed directly at window 103). The face lighting LEDs 140 are generating a face light output generally indicated by shaded rectangle 141. The face light output is directed toward the area adjacent chairs 105A-D (e.g., at least the area that would be occupied by faces of humans that are sitting in the chairs 105A-D). The state of FIG. 3 may be the desired state when individuals are sitting in one or more of the chairs 105A-D and daylight is provided through window 103 to an extent that, absent lighting from face lighting LEDs 140, would cause high contrast between entering daylight from the window 103 and the front view of the faces of the individuals sitting in the chairs 105A-D to make viewing of those faces difficult for another individual (e.g., an individual in any one of chairs 105E-H).

The face light output generated by face lighting LEDs 140 may be diffuse to minimize glare to individuals seated in chairs 105A-D. In some embodiments the face light output may have a beam angle that restricts the light output generally to areas that would be occupied by the individuals seated in chairs 105A-D. Such a beam angle may enable a substantial portion of the lumen output of the task lighting LEDs 130 to be utilized for illuminating individuals' faces seated in chairs 105A-D. In some embodiments only certain of the face lighting LEDs 130 may be illuminated to only provide illumination toward those chairs 105A-D that are actually occupied by a human. For example, if only chairs 105A and 105D are occupied (e.g., as determined by presence sensor 126) then only those LEDs of face lighting LEDs 130 which generate a light output toward chairs 105A and 105D may be illuminated. In some embodiments the light directed at a single of the chairs 105A-D may be directed at multiple portions of a person's face (e.g., the left side and right side), to increase the modeling of the face (the way the shapes and shadows are visible). For example, at least two distinct diffuse face lighting components may be directed toward an individual's face (e.g., two components primarily directed about two distinct axis spaced apart from one another and/or non-parallel to one another).

The light output of the face light output may be set as desired. For example, in some embodiments the light output intensity of the face light output may be set to achieve approximately 200 lux at a face of an individual sitting in one of the chairs 105A-D. Also, for example, in some embodiments, during an energy savings mode the light output intensity of the face light output may be set to achieve a lux value at a face of an individual sitting in one of the chairs 105A-D that is less than or equal to approximately 25% of the lux value at the table 107. For example, the controller 122 may utilize input from daylight sensor 124 to adjust the light output intensity of the face lighting LEDs 140 to generate a lux a predetermined distance away that is approximately 20% of the measured lux via daylight sensor 124. In some embodiments the light output intensity of the face light output may additionally or alternatively be adjustable (e.g., from 0% to 25% in an energy savings mode) by a user via a user interface (e.g., a dimmer) and/or automatically (e.g., proportional to brightness of daylight provided through window 103). In some embodiments the energy savings mode may be utilized during certain time periods (e.g., as set by a user via a user interface, during periods of traditionally high energy demand), may be utilized in response to a demand response event communicated to the controller 122, and/or may be utilized as one of a plurality of user selectable modes.

In some embodiments, the light output of the face light output may also be set to a light therapy mode. During the light therapy mode the light output intensity of the face light output may be set to achieve a lux value at a face of an individual sitting in one of the chairs 105A-D that is greater than the light output intensity in the energy savings mode. Other light output characteristics of the face light output may additionally or alternatively be altered in therapy mode or energy savings mode such as, for example, color, beam angle, and/or frequency. In some embodiments the light therapy mode may be utilized in situations where it is desired to reduce contrast between entering daylight from the window 103 and the front view of the faces of the individuals sitting in the chairs 105A-D to make viewing of those faces less difficult. In some embodiments the light therapy mode may be activated without regard to the daylight from the window 103. In some embodiments, during light therapy mode, only certain of the face lighting LEDs 130 may be illuminated to only provide illumination toward those chairs 105A-D that are actually occupied by a human. For example, if only chairs 105A and 105D are occupied (e.g., as determined by presence sensor 126) then only those LEDs of face lighting LEDs 140 which generate a light output toward chairs 105A and 105D may be illuminated.

In some embodiments, during light therapy mode the light output intensity of the face light output may be set to achieve a lux value at a face of an individual sitting in one of the chairs 105A-D that is less than or equal to approximately 200% of the lux value at the table 107. For example, the controller 122 may utilize input from daylight sensor 124 to adjust the light output intensity of the face lighting LEDs 140 to generate a lux a predetermined distance away that is approximately 200% of the measured lux via daylight sensor 124. In some embodiments the light output intensity of the face light output during the light therapy mode may additionally or alternatively be adjustable (e.g., from 0% to 200%) by a user via a user interface (e.g., a GUI) and/or automatically. In some embodiments the light therapy mode may be utilized during certain time periods (e.g., as set by a user via a user interface, during periods traditionally utilized for light therapy, at the beginning of a meeting). In some embodiments the light therapy mode may be utilized as one of a plurality of user selectable modes.

In some embodiments, the light therapy mode may be utilized in response to feedback from one or more sensors. For example, one or more bio-feedback signals from one or more individuals may be utilized to automatically switch on light therapy mode for the face lighting LEDs directed at those individual(s). For example, bio-feedback signals based on an analysis of video images of the eye-movements and/or pupil size may be analyzed. Accordingly, if an individual person sitting at the table is getting less concentrated or sleepy, the face lighting directed at such individual can be altered (e.g., switched to one or more higher intensities, switched to one or more different colors—optionally while maintaining face lighting levels directed at other individual(s) at another level (e.g., a different light therapy mode level, an energy savings mode level, or off completely)). In some embodiments lighting therapy may otherwise be individually tailored for one or more individuals. For example, in some embodiments a user interface may be utilized to set desired light therapy characteristics for certain chairs 105A-D. Also, for example, a user may have an RFID tag or other device that communicates desired light therapy settings to the controller 122.

Although only one side of the table 107 is provided with face lighting from face lighting LEDs 140 in the Figures, in other embodiments additional sides of the table 107 may be provided with face lighting if desired. For example, in some embodiments face lighting may be provided toward chairs 105E-H and/or toward the chair-less ends of table 107 (where individuals might stand, or sit in additional seating). Such additional face lighting may be generated by face lighting LEDs 130 of lighting fixture 120 and/or from one or more additional lighting fixtures having face lighting. Any such additional lighting fixtures may optionally be in network communication with lighting fixture 120.

Figure 4:
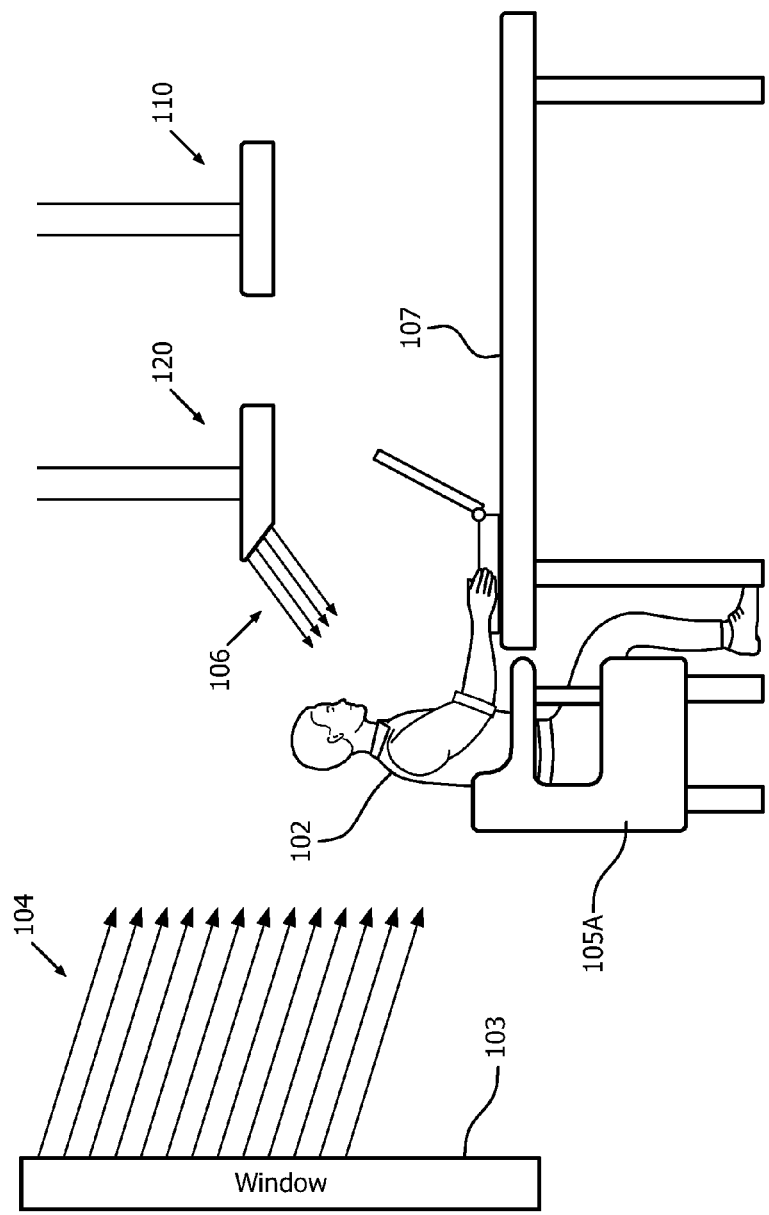
FIG. 4 illustrates a side view of the meeting room; the task lighting component of the lighting fixture with the face light component is switched off, a facial lighting component of the lighting fixture with the face light component is switched on, and the normal lighting fixture is switched off.

FIG. 4 illustrates a side view of the meeting room with the lighting fixtures 110, 120 in a state such as that shown in FIG. 3. The face lighting LEDs 140 of the lighting fixture 120 are directing face light output 106 toward the face of an individual 102 that is seated in chair 105A. The face light output 106 makes the face of the individual 102 more easily viewable by those on an opposite side of the table 107 and minimizes the contrast between daylight 104 entering through the window 103 and the front view of the face of the individual 102.

Figure 6:
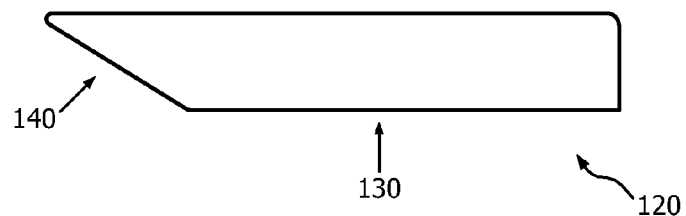
FIG. 6 illustrates a side view of the lighting fixture with the face light component of the embodiment of the lighting system of FIGS. 1-4.

FIG. 6 illustrates a side view of the lighting fixture 120. The task lighting LEDs 130 are provided on a bottom portion of the lighting fixture 120 that generally faces toward the table 107. The face lighting LEDs 140 are provided on a side portion of the lighting fixture that is positioned at an upward angle relative to the bottom portion. In some embodiments the mounting angle of the LEDs 140 may be selected to direct light output a desired extent peripherally of the lighting fixture 120. The LEDs 130 and/or 140 may be paired with one or more reflectors, diffusers, optical pieces, and/or other optical elements to achieve desired light output characteristics.

Figure 7:
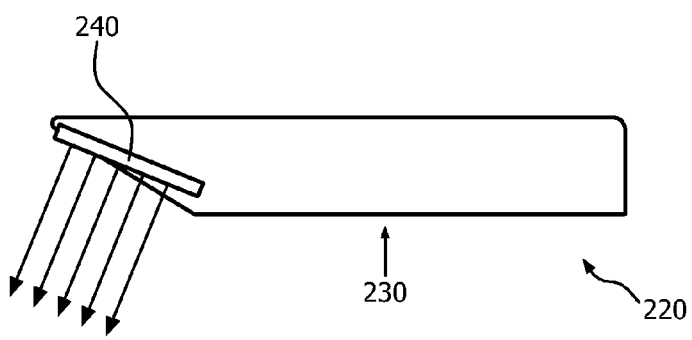
FIG. 7 illustrates another embodiment of a lighting fixture with a face light component that is directionally adjustable.

FIG. 7 illustrates another embodiment of a lighting fixture 220. The lighting fixture 220 includes task lighting LEDs 230 on a bottom portion thereof and a face light component that includes a plurality of LEDs 240 that are mechanically directionally adjustable. The directionally adjustable LEDs 240 may enable fine tuning of the illumination to be adaptable to various environments. For example, the direction of the LEDs 240 may be adjusted to accommodate different size tables, to accommodate different lighting fixture installation positions, and/or to accommodate different seating and/or standing arrangements adjacent a table or other task area. In some embodiments, all the LEDs 240 may be uniformly adjustable. In other embodiments individual segments of the LEDs 240 may be individually adjustable. For example, multiple segments may be provided, with each of the segments directed generally toward a user segment such as a chair or group of chairs and each of the segments being individually adjustable.

Figure 8:
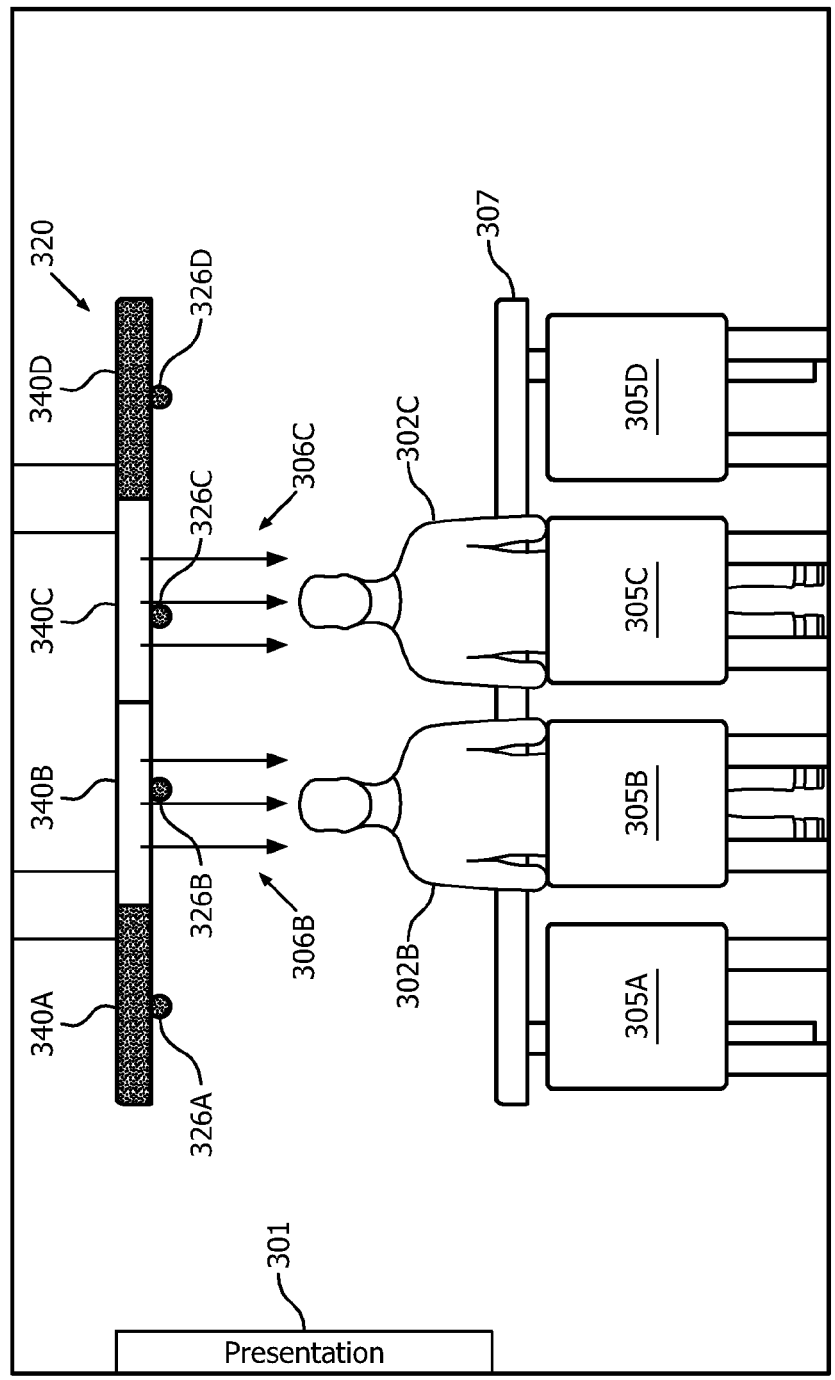
FIG. 8 illustrates another embodiment of a meeting room having another embodiment of a lighting fixture with a facial lighting component.

FIG. 8 illustrates another embodiment of a meeting room having another embodiment of a lighting fixture 320. The meeting room includes a presentation screen 201. Inside the meeting room are chairs, four of which (305A-D) are visible and two of which (305B, 305C) have individuals 302B, 302C sitting in them. A window is also present in the meeting room. The window is not illustrated but is to the rear of the two individuals 202B, 202C (in other words, in a direction out of the page). Natural daylight from the outside environment may pass through the window and provide lighting to portions of the meeting room.

The lighting fixture 320 includes face lighting including a first face lighting segment 340A, a second face lighting segment 340B, a third face lighting segment 340C, and a fourth face lighting segment 340D. Four presence sensors 326A, 326B, 326C, and 326D are also provided, each being paired with a respective of the face lighting segments 340A-D. The presence sensor 326A monitors for presence of an individual in seat 305A, the presence sensor 326B monitors for presence of an individual in seat 305B, the presence sensor 326C monitors for presence of an individual in seat 305C, and the presence sensor 326D monitors for presence of an individual in seat 305D. Since nobody is present in seats 305A or 305D the lighting segments 340A and 340D are not generating a light output. Since individuals 302B and 302C are present in seats 305A and 305D, lighting segments 340B and 340C are illuminated and directing light output 306B and 306C toward the faces of the individuals 302B, 302C.

One or more controllers may be in communication with the presence sensors 326A-D and utilize output therefrom to control which face lighting segments 340A-D are illuminated. The segments 340A-D may optionally be operable in an energy savings mode and/or a light therapy mode as described herein for example with respect to lighting fixture 120. The face lighting segments 340A-D may additionally or alternatively optionally be adjusted and/or activated based at least in part on readings from one or more daylight sensors as described herein for example with respect to lighting fixture 120. The lighting fixture 320 may also optionally incorporate a task lighting component including one or more task lighting sources as described herein for example with respect to lighting fixture 120.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrases "and/or" and "or" as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements.

It should also be understood that, unless clearly indicated to the contrary, in any methods claimed herein that include more than one step or act, the order of the steps or acts of the method is not necessarily limited to the order in which the steps or acts of the method are recited. Any reference numerals appearing between parentheses in the claims, if any, are provided merely for convenience and should not be construed as limiting the claims in any way.

The invention claimed is:

1. A method of controlling a task lighting component and a face lighting component of at least one lighting fixture, comprising:

monitoring a light level proximal to a task area;
providing task lighting from at least one lighting fixture over said task area to said task area based on said light level proximal to said task area;
monitoring each of a plurality of user segments for a human presence, said user segments adjacent said task area and utilized for user interaction with said task area; and
providing face lighting from said at least one lighting fixture over said task area to a given user segment of said user segments based on said given user segment having said human presence;
wherein one or more characteristics of said face g and said task lighting are adjustable independently from each other.

2. The method of claim 1, wherein in a first mode, only said user segments having said human presence and interposed between said task area and a window contributing to said light level are provided with said face lighting.

3. The method of claim 2, wherein in a second mode, all said user segments having said human presence are provided with said face lighting.

4. The method of claim 3, wherein in said first mode, a ratio of a face surface lux to a task surface lux is less than one, said face surface lux taken at a face surface in each of said user segments and said task surface lux taken at said task surface, and wherein in said second mode, said ratio of said face surface lux to said task surface lux is tunable within a second range, said second range including values greater than one.

5. The method of claim 1, wherein said task lighting is generated from a first group of LEDs facing said task area and said face lighting is generated from a second group of LEDs facing user segments.

6. The method of claim 1, wherein the one or more characteristics of said face lighting and said task lighting that are adjustable independently from each other are selected from the group consisting of: intensity, spectral composition, and dynamic behavior.

7. The method of claim 1, wherein providing said face lighting from said at least one lighting fixture over said task area to a given user segment of said user segments based on said given user segment having said human presence includes providing said face lighting to only said user segments having said human presence.

8. The method of claim 1, wherein providing said task lighting from said at least one lighting fixture over said task area to said task area based on said light level proximal said task area includes providing said task lighting only when said light level is below a threshold value.

9. The method of claim 1, wherein said task lighting is distinct from said face lighting in at least one of intensity, spectral composition, and dynamic behavior.

10. The method of claim 9, wherein said characteristics of said face lighting can be set independently for at least one of said user segments via a user interface.

11. The method of claim 1, wherein, in response to identifying at least one of a predetermined intensity of incoming daylight and a predetermined direction of said incoming daylight, said face lighting is automatically provided to said user segments that are on the side of said lighting fixture where said daylight originates.

12. The method of claim 1, wherein providing said task lighting based on said light level proximal said task area includes providing a task lighting level of said task lighting that is proportional to said light level proximal said task area.

13. The method of claim 1, wherein an origination direction of said face lighting directed toward each of said user segments is adjustable.

14. The method of claim 1, wherein an origination direction of said face lighting directed toward each of said user segments includes at least a first component primarily directed about a first axis and a second component primarily directed about a second axis.

15. The method of claim 1, wherein said step of monitoring each of said user segments includes monitoring reflections of coded light directed at each of said user segments.

16. The method of claim 1, wherein each of said user segments include at least one chair sitting area adjacent said task area.

17. The method of claim 1, wherein said characteristics of said task lighting are adjusted based on first criteria and said characteristics of said face lighting are adjusted based on second criteria, said second criteria unique from said first criteria.

18. At least one lighting fixture, the at least one lighting fixture comprising:
a task lighting component configured to provide task lighting over a task area based on a light level monitored proximal to said task area; and
a face lighting component providing face lighting over said task area to a given user segment of each of a plurality of user segments based on monitoring of each of the plurality of user segments for a human presence, said user segments adjacent said task area and utilized for user interaction with said task area, and said given user segment having said human presence, wherein one or more characteristics of said face lighting and said task lighting are adjustable independently from each other.

* * * * *